(12) United States Patent
Kumar et al.

(10) Patent No.: US 6,560,483 B1
(45) Date of Patent: May 6, 2003

(54) IONTOPHORETIC DELIVERY PATCH

(75) Inventors: Matthew M. Kumar, Oronoco, MN (US); Larry D. Johnson, Cannon Falls, MN (US)

(73) Assignee: Minnesota High-Tech Resources, LLC, Red Wing, MN (US)

( * ) Notice: Subject to any disclaimer, the term of this patent is extended or adjusted under 35 U.S.C. 154(b) by 83 days.

(21) Appl. No.: 09/691,312

(22) Filed: Oct. 18, 2000

(51) Int. Cl.[7] ................................................. A61N 1/30
(52) U.S. Cl. ............................................ 604/20; 604/501
(58) Field of Search ........................... 604/20, 501, 500, 604/289, 890.1

(56) References Cited

U.S. PATENT DOCUMENTS

| | | | |
|---|---|---|---|
| 4,542,013 A | 9/1985 | Keith | 424/28 |
| 4,702,732 A | 10/1987 | Powers et al. | 604/20 |
| 5,458,569 A | 10/1995 | Kirk, III et al. | 604/20 |
| 5,589,180 A | 12/1996 | Hind | 424/402 |
| 5,651,768 A | 7/1997 | Sibalis | 604/20 |
| 5,682,726 A | 11/1997 | Green et al. | 53/433 |
| 5,688,231 A | 11/1997 | Flower | 604/20 |
| 5,709,869 A | 1/1998 | Hind | 424/402 |
| 5,830,175 A | 11/1998 | Flower | 604/20 |
| 5,876,368 A | 3/1999 | Flower | 604/20 |
| 6,009,344 A | 12/1999 | Flower et al. | 604/20 |
| 6,018,679 A | 1/2000 | Dinh et al. | 604/20 |
| 6,018,680 A | 1/2000 | Flower | 604/20 |
| 6,024,975 A | 2/2000 | D'Angelo et al. | 424/449 |
| 6,038,464 A | 3/2000 | Axelgaard et al. | 600/391 |
| 6,047,208 A | 4/2000 | Flower | 604/20 |
| 6,167,302 A | * 12/2000 | Millot | 604/20 |
| 6,383,511 B1 | * 5/2002 | Cassel | 424/448 |

* cited by examiner

*Primary Examiner*—Edward K. Look
*Assistant Examiner*—Kimya N McCoy
(74) *Attorney, Agent, or Firm*—Fredrikson & Byron, P.A.

(57) ABSTRACT

A patch for iontophoretic transdermal application of a medicant, where the patch includes a border portion disposed about an aperture. The border portion can include a first polarity electrode in electrical communication with the medicant, and a second border portion including a second electrode having a second polarity opposite the first electrode polarity. One patch has a liftable cover, preferably a transparent and non-adherent cover, disposed over the patch aperture. A preferred medicant for inclusion in the present invention is a local anesthetic or analgesic. Other medicants such as anti-inflammatory agents or anti-infective agents may be used to locally reduce inflammation, contain infection, and alleviate pain. The present invention can allow performing a field block anesthetic about an epidermal target site. The present invention can allow observing a target or treatment site while leaving the patch in place. An invasive medical procedure can be performed through the patch aperture, and pre-operative and post-operative procedures can also be performed through the patch aperture.

43 Claims, 3 Drawing Sheets

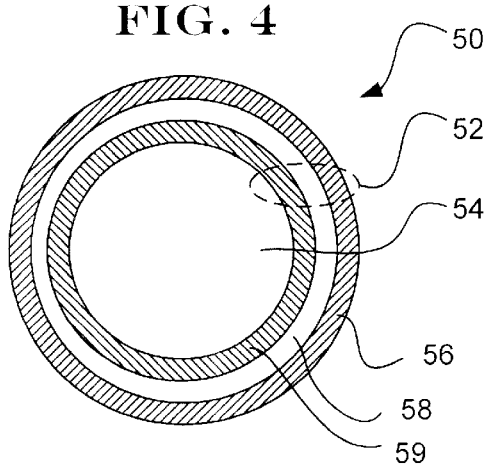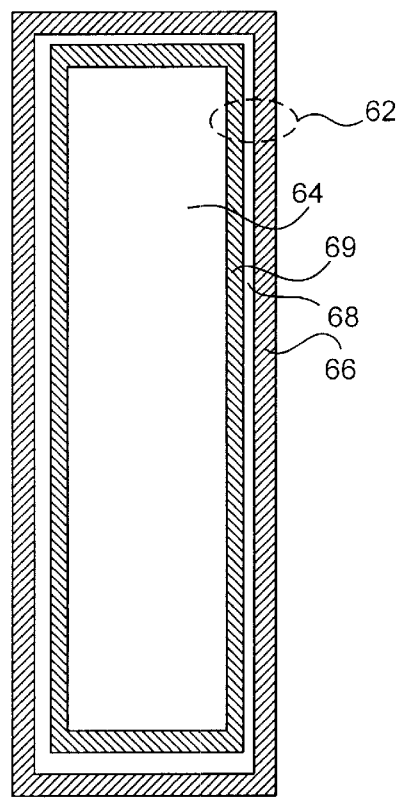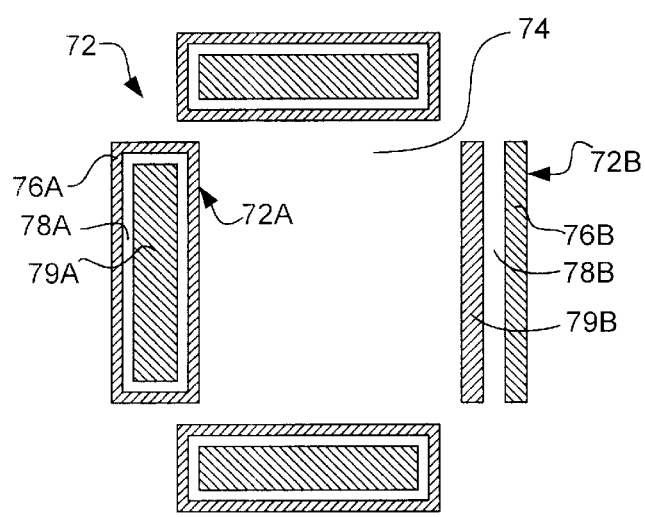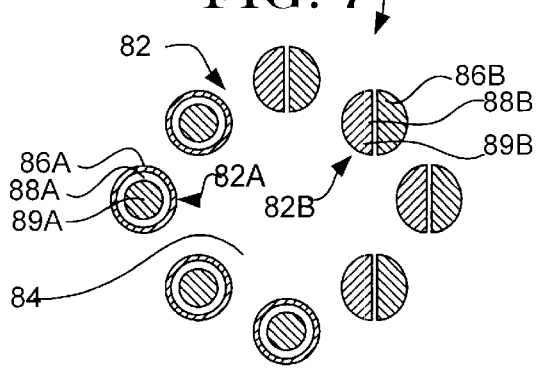

IONTOPHORETIC DELIVERY PATCH

FIELD OF THE INVENTION

The present invention is related generally to medical devices. More specifically, the present invention is related to skin patches for drug or medicant delivery.

BACKGROUND OF THE INVENTION

Systems for delivering ionized drugs through the skin have been known for many years. The application of an electrical field to the skin has been found to greatly enhance the skin's permeability to various ionic agents. In general, iontophoretic methods include the introduction of various ions into tissues through the skin by means of electricity. Additionally, applying an electrical current to the area around a wound has been found to improve wound healing. Iontophoretic techniques have been used to deliver some drugs, thus eliminating the requirement for hypodermically injecting these drugs. The elimination of the requirement for hypodermic injection can reduce or eliminate the associated problems of pain, trauma, and infection to the patient.

The manufacture and use of conventional iontophoretic patches is well known to those skilled in the art. In particular, Flower discusses iontophoretic controllers, patches, and electrodes in U.S. Pat. Nos. 5,668,231, 5,830,175, 5,876,368, 6,009,344, 6,047,208, and 6,018,680. Manufacture of patches is discussed by Green et al. in U.S. Pat. No. 5,682,726. Electrodes and patch discussions are included in U.S. Pat. No. 5,651,768 (Sibalis), U.S. Pat. No. 6,038,464 (Axelgaard et al.), and U.S. Pat. No. 5,458,569 (Kirk, III et al.). Iontophoresis, including polymeric carriers, delivery vehicles, and medicants, are discussed by Keith in U.S. Pat. No. 4,542,013, by D'Angelo et al. in U.S. Pat. No. 6,024,975, and by Powers et al. in U.S. Pat. No. 4,702,732. All of the aforementioned patents, which include subject matter in addition to that specifically cited above, are herein incorporated by reference in their entirety.

Iontophoresis is an active method for transdermal delivery of medicants. Active delivery methods may be distinguished from passive delivery methods. Passive methods rely on natural forces and pressures alone such as diffusion or concentration gradients. Conventional drug delivery skin patches are examples of passive delivery vehicles. Active methods use externally applied forces, for example, electrical potential or hydraulic forces, to force a medicant into the skin. Iontophoretic patches are active delivery vehicles for medicants.

Prior art iontophoretic analgesic or anesthetic devices have been limited in use to broad area application of an anesthetizing agent, for example, an anesthetic gel. One drawback of existing devices is that they must be applied directly over the target area. This has been undesirable as the target area cannot be viewed during application of the anesthetic, and the patch must be removed to view the target area. Once the patch is removed to access the site, delivery of the anesthetic stops. This creates a likelihood that the anesthesia will wear off as the procedure progresses, causing increased pain. In order to continue, the treating physician must either reapply the patch and wait for it to take effect, inject the site with local anesthetic, continue the procedure in spite of the increasing pain, or convert to general anesthesia.

Another problem with prior art devices, where the target area includes a wound, is that the anesthetic gel is placed directly on the target area. This creates a possibility that the anesthetic gel will contaminate the wound, cause infection or inflammation, or hinder the healing of the wound. One prior art method avoids this problem by using a field block. Local anesthesia may be achieved by making several injections in the area surrounding the target site, thus creating what is commonly referred to as a field block. A field block procedure may be fairly painful in itself, and may traumatize the patient, particularly a child.

After removal of prior art delivery patches, or after completion of the field block, there is no fail-safe method for determining where the anesthetized area begins or ends. This creates the potential for continuing a procedure into an un-anesthetized area, causing pain to the patient.

What would be desirable is a medical device capable performing local anesthesia without many of the aforementioned limitations.

SUMMARY OF THE INVENTION

The present invention includes a patch for transdermal application of a medicant, where the patch includes a border portion disposed about an aperture. The border portion can include a first polarity electrode in electrical communication with the medicant, and a second electrode having a second polarity opposite the first electrode polarity. One patch has a liftable cover, preferably a transparent and non-adherent cover, disposed over the patch aperture. A preferred medicant for inclusion in the present invention is a local anesthetic or analgesic. Some embodiments have single-part electrodes disposed on one side of the opposite polarity electrode, while other embodiments have two-part electrodes, with each part disposed on opposite sides of the opposite polarity electrode. Another embodiment includes a single polarity patch electrode to be used with an opposite polarity external electrode.

The present invention allows for performing a field block anesthetic about an epidermal target site. Patches according to the present invention can be used to actively deliver an anesthetic substance to a region bordering the target site, without requiring delivery under fluid pressure, or delivery requiring mechanical penetration, into the epidermis.

The present invention allows for observing a target or treatment site while leaving the patch in place. An invasive medical procedure can be performed through the patch aperture, and pre-operative and post-operative procedures can also be performed through the patch aperture. In one application of the present invention, local anesthetic may be iontophoretically applied around a burn or wound, allowing for pain management local to the wound, while leaving the wound observable and treatable through a liftable, transparent cover. In another application of the present invention, an iontophoretic patch may be applied, and anesthetic delivered before, during, and after a surgical incision, with the incision wound observable after the procedure through a transparent, liftable cover.

BRIEF DESCRIPTION OF THE DRAWINGS

FIG. 4 is a highly diagrammatic top view of an iontophoretic delivery patch having a contiguous border first polarity electrode disposed within a contiguous second polarity electrode;

FIG. 5 is a highly diagrammatic top view of a iontophoretic delivery patch having a contiguous border first polarity electrode disposed within a contiguous second polarity electrode;

FIG. 6 is a highly diagrammatic top view of a iontophoretic delivery patch having a discontiguous border electrode of two different types disposed about an aperture;

FIG. 7 is a highly diagrammatic top view of an iontophoretic delivery patch having a discontiguous border electrode of two different types disposed about an aperture.

DETAILED DESCRIPTION OF THE INVENTION

Figure 1:
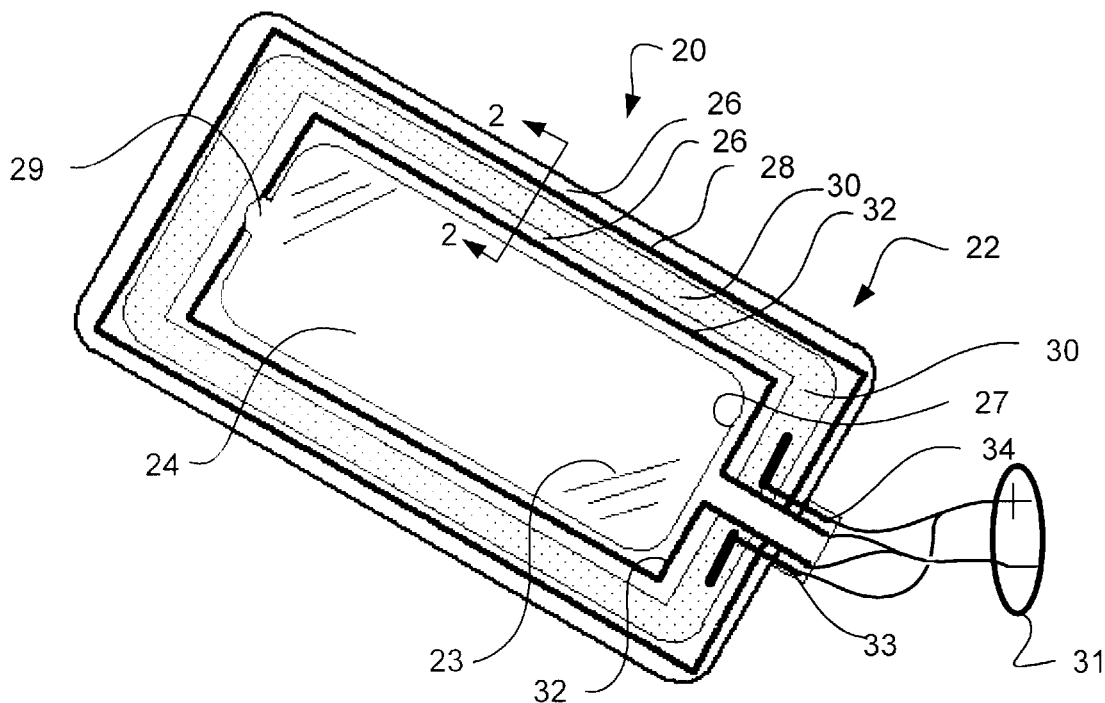
FIG. 1 is perspective view of an iontophoretic delivery patch having a medicant delivering border region disposed about a central aperture, with the border region having a first polarity electrode disposed between two parts of a second polarity electrode.

In the invention examples discussed below, similar reference numerals refer to similar elements in the various embodiments and Figures referenced. FIG. 1 illustrates an iontophoretic delivery patch 20 including a border region 22 disposed about an aperture region 24. The terms "border" and "border region", as used herein, refer to borders having width. Border region 22 includes a first pair of electrodes 33 and 34, both in electrical communication with a medicant carrying gel 30, and both having a first electrical polarity. Gel 30 is preferably a carrier for a local anesthetic. Border region 22 also includes a second polarity electrode, having an inner electrode 32 and an outer electrode 28. Gel 30 is illustrated as separated from second polarity electrodes 28 and 32 by insulating region or insulator 26. An electrical potential source 31 is shown, which may include a battery intended to be discarded with the patch. Iontophoretic patch electrical potential sources are well known to those skilled in the art.

In the embodiment illustrated in FIG. 1, aperture 24 has a cover 23 draped over the aperture. In one embodiment, cover 23 is liftably removable from border region 22. One example of the invention has cover 23 formed of a transparent material, joined along a first edge 27, and graspable with a lifting tab 29. Another embodiment of the invention has a completely removable cover. The cover can be formed of a removable membrane that can be coated with a biocompatible adhesive. The transparent and removable membrane preferably does not contain any medication or conduct electrical current.

In one embodiment of the invention, insulating region 26 includes an insulating material, while in another embodiment of the invention, insulating region 26 is an open air space between the gel and the second electrode. In the embodiment illustrated in FIG. 1, first electrodes 33 and 34 actually extend over the surface of gel 30, but have been shown as cut-away to illustrate the gel beneath. In another embodiment of the invention, the first electrodes do not extend around the entire border region, and the medicant carrying material is sufficiently conductive to serve as an electrode.

It should be understood that a patch according to the present invention can have any convenient size or shape, for example, square, rectangular, oval, circular, or tailored for a specific location on the skin. In a preferred embodiment, the periphery is raised to accommodate a reservoir for an anesthetizing agent and electrodes.

Figure 2:
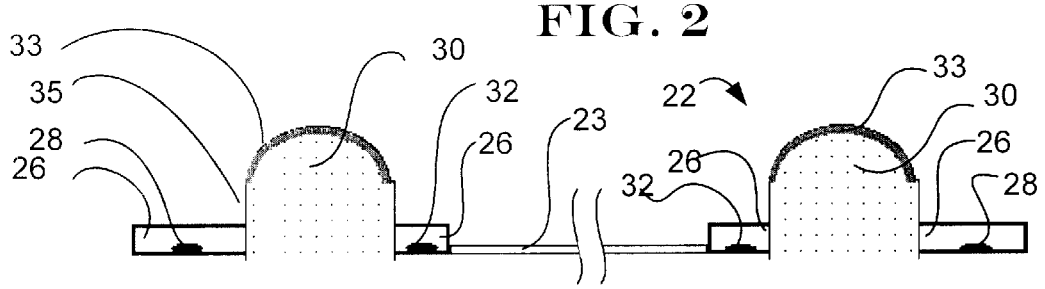
FIG. 2 is a transverse, cross-sectional view taken through 2—2 of FIG. 1, illustrating a first polarity gel electrode disposed between two parts of a second polarity electrode.

FIG. 2 illustrates a cross section of patch 20 of FIG. 1 taken through 2—2, illustrating further first polarity electrode 33 disposed over medicant carrying gel 30, which is contained within a reservoir wall 35. Second polarity electrodes 28 and 32 are shown disposed within an insulator 26, insulating the second polarity electrodes from first polarity electrode 33 and gel 30. In one embodiment, insulator 26 is an insulating solid, while in another embodiment, insulator 26 is effectively air, with the second polarity electrodes adhesively applied directly to the skin. Aperture 24 may be seen between border regions 22, and having cover 27 draped thereover.

Figure 3:
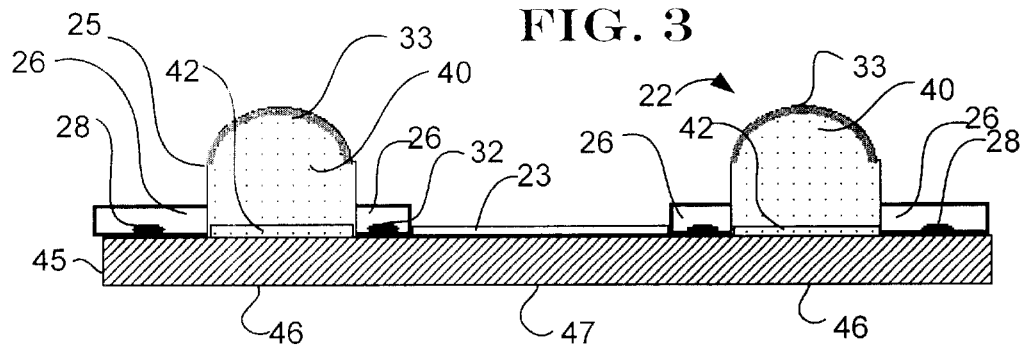
FIG. 3 is a transverse, cross-sectional view similar to the view of FIG. 2, but illustrating a membrane bound, first polarity liquid reservoir electrode disposed between two parts of a second polarity electrode.

In FIG. 3, a patch has been applied to skin or epidermal region 45, having a target site 47 surrounded by a border region 46. FIG. 3 illustrates a view taken through a patch similar to that of FIG. 1, and through a section somewhat similar to 2—2, but having a liquid medicant carrier 40 bounded by a reservoir wall 25 and by a microporous or semi-permeable membrane 42. The medication can migrate through membrane 42 to be deposited in the skin. The membrane may not be needed, depending on the nature of the medication in the reservoir. Some medications suspended in a gel do not require a membrane. In some embodiments, medications in a gel form are in direct contact with the skin, not requiring containment by a membrane.

The medicant carrying layers 30 and 40 of FIGS. 2 and 3 may consist of a flexible pouch or reservoir containing the drug to be administered. As well known to those skilled in the art, the reservoir can contain a drug of choice in suspension or solution, with walls dense enough to prevent leakage, but sufficiently porous to permit migration of the charged particles or ions under the influence of the electrical charge imposed.

An electrically conductive adhesive material may also be used to coat the underside of parts of the border regions of the devices so that they may be placed on and adhered to the skin, and make good electrical contact with the skin. The adhesive can be be any suitable material, preferably comfortable to the wearer, that permits the device to be bent and formed to fit snuggly to the contour of the target area.

It may be seen from inspection of FIGS. 2 and 3 that electrodes 28 and 32 may be used to electrically charge the skin, creating an electrical potential between combined electrodes 28 and 32, and electrode 33 in contact with the medicant to be delivered. It may also be seen that the above described arrangement in general forms a complete electric circuit from one side of the electrical source, to one electrode, medication carrier, microporous membrane, adhesive material, skin, adhesive material, second electrode, and back to the electrical source.

A local anesthetic gel may be contained in a plastic dome that extends around the periphery of the patch. See, for example, curved wall 35 of FIGS. 2 and 3. The dome can be a few millimeters to centimeters high, and a few millimeters to centimeters wide. The inside roof of the dome may contain an electroconductive material, which may be sprayed on the plastic or attached by adhesive. This conductive material can act as the principal electrode that can be connected to an external power source. When electrified, this conductive material conducts electricity to the local anesthetic gel. When this invention is applied to the body surface, the local anesthetic gel is in contact with the skin or the mucus membrane, and permits the diffusion of local anesthetic into the contacting skin or mucus membrane.

The present invention may lie against the skin using patch material including nonconductive, medical grade, closed cell foam material such as cross-linked polyethylene, polyester felt, or any other similar material that will be known to those skilled in the art. Patch material may range from a few microns to a few millimeter in thickness in some embodiments. The present invention has a central window or aperture that may be covered by an adhesive or nonadhesive transparent membrane. A patch according to the present invention, when applied to the body surface, may hold a local anesthetic reservoir firmly against the body surface. This permits the local anesthetic contained in the reservoir to stay in contact with the skin or the mucus membrane. An adhesive on the underside of this invention may also hold a strip of conductive material serving as an electrode, on either side of the reservoir, firmly in contact with the skin or mucus membrane. The adhesive may thus form the insulator insulating the electrodes of opposite polarities from each other.

FIG. 4 illustrates another embodiment of the invention in a patch 50 formed generally of a contiguous border indicated at 52 disposed about an aperture 54. Border 52 includes a first polarity electrode 56 disposed about an insulator 58 disposed about a second polarity electrode 59. A medicant, for example an analgesic, may be disposed at either first electrode 56 or second electrode 59. Patch 50 includes only a single part first electrode and a single part second electrode, unlike patch 20 of FIG. 1.

FIG. 5 illustrates another embodiment of the invention in a patch 60 formed generally of a contiguous border indicated at 62 disposed about an aperture 64. Border 62 includes a first polarity electrode 66 disposed about an insulator 68 disposed about a second polarity electrode 69. A medicant, for example a local anesthetic or analgesic, may be disposed at either first electrode 66 or second electrode 69.

FIG. 6 illustrates yet another embodiment of the invention in a patch 70 formed generally of a discontiguous border indicated at 72 disposed about an aperture 74. Border 72 illustrates the discontiguous border aspect of this embodiment. A preferred embodiment has a contiguous border, but gaps in the border are possible, provided electrical potential is provided to the discontiguous segments. Border region 72 is formed of a first border segment type 72A and a second border segment type 72B. In a preferred embodiment, a patch is formed of the same border types throughout. Border first segment type 72A includes a first polarity electrode 76A disposed about an insulator 78A disposed about a second polarity electrode 79A. A medicant, for example an anesthetic, may be disposed at either first electrode 76A or second electrode 79A. Border second segment type 72B includes a first polarity electrode 76B disposed about an insulator 78B disposed about a second polarity electrode 79B. A medicant, for example an anesthetic, may be disposed at either first electrode 76B or second electrode 79B.

FIG. 7 illustrates another embodiment of the invention in a patch 80 formed generally of a discontiguous border indicated at 82 disposed about an aperture 84. Border 82 illustrates the discontiguous border aspect of this embodiment. A preferred embodiment has a contiguous border, but gaps in the border are possible, provided electrical potential is provided to the discontiguous segments. Border 82 is formed of a first border segment type 82A and a second border segment type 82B. In a preferred embodiment, a patch is formed of the same border types throughout.

Border first segment type 82A includes a first polarity electrode 86A disposed about an insulator 88A disposed about a second polarity electrode 89A. A medicant, for example an analgesic, may be disposed at either first electrode 86A or second electrode 89A. Border second segment type 82B includes a first polarity electrode 86B disposed about an insulator 88B disposed about a second polarity electrode 89B. A medicant, for example an analgesic, may be disposed at either first electrode 86B or second electrode 89B.

Figure 8:
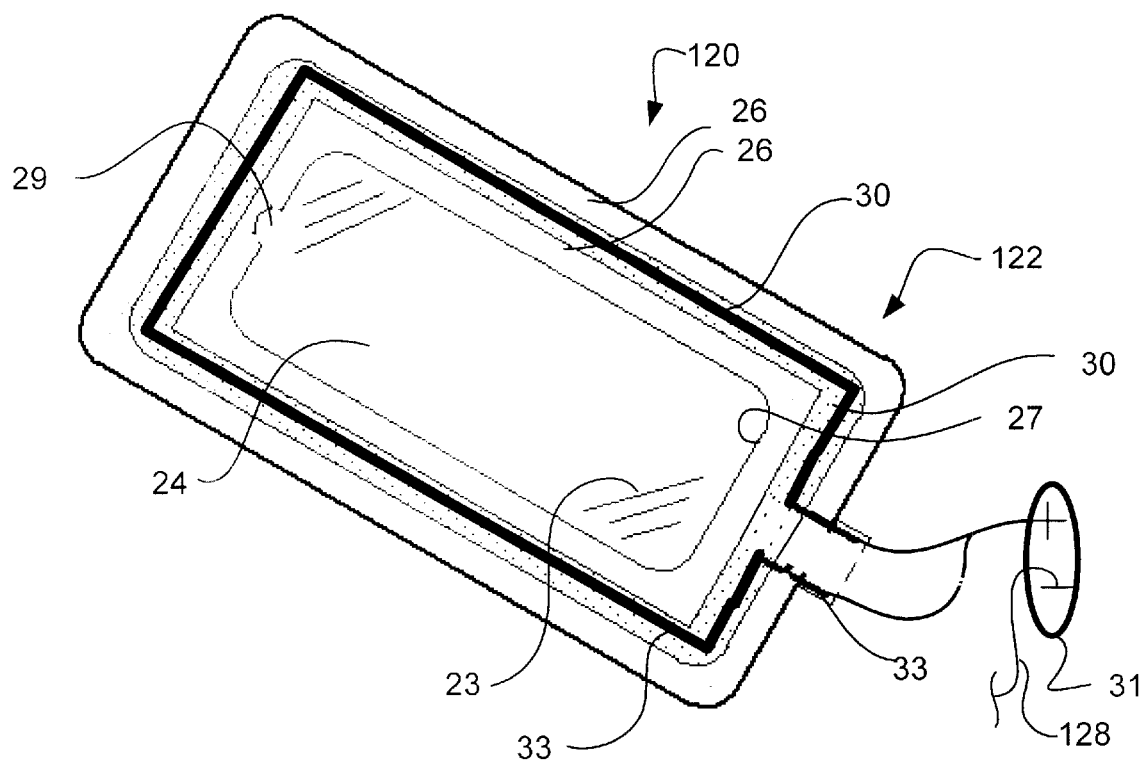
FIG. 8 is perspective view of an iontophoretic delivery patch having a medicant delivering border region disposed about a central aperture, with the border region having a first polarity electrode, the patch being suitable for use with a second electrode.

FIG. 8 illustrates an iontophoretic delivery patch 120 which is similar in many respects to patch 20 illustrated in FIG. 1. Reference numerals in FIG. 8 similar to those in FIG. 1 refer to similar elements, previously discussed with respect to FIG. 1. Patch 120 includes a border region 122 disposed about aperture region 24. Border region 122 includes first electrode 33 in electrical communication with medicant carrying gel 30, and having a first electrical polarity. Border region 122 does not includes the second polarity electrode of FIG. 1. Instead, patch 120 can be used in conjunction with a separate grounding electrode. A second polarity electrode wire 128 is partially illustrated, which can be coupled to a grounding electrode. The separate grounding electrode can be disposed either close to patch 120 on the body or disposed further away. In a preferred use of the invention, the grounding electrode is disposed close to patch 120.

The materials used to make patches according to the present invention may include nonconductive, nontoxic, flexible material. One material includes non-woven polyester felt. The patch may be coated on the underside with an adhesive composed of poly-isobutylene and colloidal silicone dioxide. The under side of the patch may also be covered with a sheet of nonstick synthetic material, which may be peeled off prior to application of the patch on to the skin. This nonstick material may include a polyethylene terephthalate (PET) film release liner. Another protective liner can include a fluorocarbon diacrylate coated polyester sheet. This liner may be removed before application.

Electrical potential devices which are believed suitable for use with patches according to the present invention can include battery-operated devices capable of delivering electrical current in a pulsatile or continuous fashion in varying magnitude and duration. Some commercial devices include: the DYNAPHOR™, a battery operated iontophoresis device available from Henley International, Sugarland, Tex.; the IONTOPHOR, a computerized, programmable, battery operated iontophoresis device available from Life-Tech Corp., Houston, Tex.; and the SP-2, a low-voltage generator unit from TECA Corp., Pleasantville, N.Y.

A polymeric diffusion matrix may be provided for the transdermal systemic delivery of medicants through the skin of a patient. The polymeric diffusion matrix may include a first lower molecular weight, partially hydrolyzed polyvinyl alcohol component, a second higher molecular weight, essentially fully hydrolyzed polyvinyl alcohol component, and glycerol.

In one embodiment, the medicant delivered in the above-described patches is a local anesthetic. Any local anesthetic agent, for example lidocaine, bupivacaine, mepivacaine, tetracaine, procaine, chloroprocaine, cocaine, or prilocaine may be used as the principal local anesthetic. The patch may contain a hydrophilic gel including the local anesthetic agent. The gel may contain varying concentrations of the local anesthetic agent. For example, the gel can contain lidocaine 4% or prilocaine 2%. A local anesthetic may be the sole agent, or two or more local anesthetics of varying concentrations may be combined to form a mixture. A mixture may be used to increase the local anesthetic efficiency, without increasing the toxicity of any one individual agent.

The medicant may include pharmaceutical agents that increase the efficiency of local anesthetics, prolong the duration of action of local anesthetics, or change the acidity of the local anesthetics, and may also be added to a local anesthetic gel. Vasoconstrictors, for example, epinephrine, phenylephrine, or ephedrine may be added to the medicant to prolong the duration of action of the local anesthetic. Acidifying or alkalizing salts may be added to the medicant to change the pH and Pka of the local anesthetics. Such alterations of pH and Pka may alter the amount of local anesthetic that can ionize and change the concentration of local anesthetic that diffuses across the skin or mucus membrane. Narcotic agents such as morphine, codeine, Demerol, fentanyl, alfentanyl, remifentanyl and sufentanyl, may be added to the gel to obtain a synergistic effect on the blockade of pain conduction from the peripheral site. Other agents such as clonidine, which are often added to spinal or epidural anesthesia to prolong the duration or increase the intensity of local anesthetic effect, may also be added to a local anesthetic in this invention.

The formulation of local anesthetic or other medications into a gel form can be accomplished by means known to those skilled in the art. For example, lidocaine may be gelled with mixing varying amounts of water and hydroxypropyl cellulose. Another gelling agent is hydroxypropylmethylcellulose. Preservatives, such as methylparaben, or propylparaben, may be added to the gel to inhibit bacterial growth. The pH and PKa may be adjusted using sodium hydroxide or hydrochloric acid.

Other medications such as salicylates, corticosteroids, or antibiotics may be added to the patch to reduce inflammation and infection at the target site. Pain may be reduced and healing enhanced. These medications may be mixed with local anesthetic agents, or administered by themselves. Such delivery of anti-inflammatory drugs or antibiotics may reduce the need for systemic administration of these agents.

The grounding electrodes, such as electrodes 26 and 28 of FIGS. 1–3, may be made of a conductive material, such as carbon filled vinyl or carbon filled rubber material. The underside of the electrodes can be coated with a conductive adhesive such as materials loaded with graphite or an ionic substance. Electrodes can be on either side of the local anesthetic reservoir. The electrodes may vary in width and thickness, for example, from a few micrometers to a few millimeters. The grounding electrodes can be connected to an external power source.

The patch central aperture in this invention may be covered by a removable transparent membrane, such as Tegaderm (R), available from 3 M Corporation. The under surface of the transparent membrane can contain a biocompatible adhesive, while the top surface is preferably free of any adhesives. The transparent membrane may be peeled off by pulling on a tab at one end of the transparent membrane. There is preferably no anesthetizing agent applied to the transparent membrane.

USES OF THE PRESENT INVENTION

The following, non-exhaustive list of methods may be practiced using the present invention, and are explicitly within the scope of the present invention.

Surgery

The present invention can be used to anesthetize skin and mucus membranes for different surgical and invasive procedures. This includes, without limitation, incision, excision, puncture, abrasion, slicing, dissecting, and approximation of cut edges by suture, staples or adhesives.

Excision of Surface Lesions

Small lesions of skin and mucus membrane, for example, cancer, moles, nevus, and cysts, can be excised painlessly following application of the present invention.

Incision and Drainage

Abscesses, hematomas, and other subcutaneous and deeper fluid collections can be drained painlessly following application of this invention.

Punctures

Procedures such as vena puncture, arterial puncture and nerve blocks can be performed painlessly after the application of this invention. This invention would be particularly useful in children who are averse to painful needle sticks.

Skin and Mucus Membrane Abrasion

The skin and mucus membrane can be abraded using mechanical devices, electricity, or laser to obliterate hair, tattoos, scars, cancer, and other surface lesions painlessly following application of this invention.

Approximation of Skin and Mucus Membrane

Lacerated or cut edges of skin and mucus membrane can be painlessly approximated using sutures, staples or adhesives painlessly following application of this invention.

Surgeries on Deeper Tissues

This invention permits painless injections of local anesthetics to numb deeper tissues. Through the removable transparent membrane, the surgeon can insert a needle in a painless fashion and infiltrate local anesthetic solutions into deeper tissue planes. This technique permits the surgeon to access deeper body tissues that lie beneath the skin and mucus membrane. Body cavities, such as abdomen, thorax, spine and cranium, along with muscles, bones and joints, can be accessed by this technique.

Postoperative Pain Control

Patches according to the present invention may be applied over surgical wounds and incisions to reduce pain. The central removable transparent membrane of some embodiments of the invention permits the caregiver to inspect and treat the wound without having to disrupt the analgesia provided by the patch. The wound or the incision may be cleaned, sutures removed, and/or antiseptics and dressing applied. These procedures can be done without interfering with the delivery of the analgesia provided by this invention. This invention is particularly useful for postoperative wound care in children. The patch reduces the amount of systemic painkillers, such as morphine, Demerol, aspirin or Tylenol, which a patient might need. Reduction in pain and a reduction in systemic pain medication permit the patient to be out of bed sooner.

Painful Skin and Mucus Membrane Lesions

The present invention may also be used to control pain originating from skin and/or mucus membrane due to a variety of causes. This includes traumatic injuries, abrasions, lacerations, punctures, burns, and infections. This invention permits observation and treatment of the painful lesion through the removable transparent membrane, without interfering with the delivery of the analgesia.

Enhanced Wound Healing

Applicants also believe that electrical potential applied to the skin surrounding an incision or wound, may per se hasten wound healing and alleviate pain. This effect may be unrelated to medications contained in the patch. Unlike some prior art devices, where opposite electrodes are placed on either sides of a wound to create an electrical potential across the wound, one embodiment of the present invention requires no such potential to be created across the wound. Instead, in this embodiment, both electrodes are on the same side of the wound, in an encircling fashion, creating an electrical field around the wound. The encircling electrical field may stimulate the nerve endings, release endorphins and enhance the blood supply to the wound, allowing it to heal faster and reduce pain.

Human and Animal Use

The present invention may be used to treat both humans and animals. Veterinary applications are explicitly within the scope of the present invention.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A patch for transdermal application of a medicant comprising:
   a patch border portion disposed about an aperture;
   said border portion including a first polarity electrode disposed about said aperture and disposed to be in electrical communication with said medicant;
   said border portion including a second electrode disposed about said aperture and having a polarity opposite said first electrode, said second electrode being electrically separated from said first electrode.

2. A patch for transdermal application of a medicant as in claim 1, further comprising a liftable portion disposed over said aperture.

3. A patch for transdermal application of a medicant as in claim 2, wherein said liftable portion is removable.

4. A patch for transdermal application of a medicant as in claim 2, wherein said liftable portion has a periphery and said liftable portion is attached to said patch border along at least one portion of said periphery.

5. A patch for transdermal application of a medicant as in claim 2, wherein said patch liftable portion is transparent.

6. A patch for transdermal application of a medicant as in claim 2, wherein said patch liftable portion is non-adherent to skin.

7. A patch for transdermal application of a medicant as in claim 2, wherein said patch border portion is contiguous.

8. A patch for transdermal application of a medicant as in claim 2, wherein said patch border portion includes non-contiguous border segments.

9. A patch for transdermal application of a medicant as in claim 2, wherein said medicant includes an analgesic.

10. A patch for transdermal application of a medicant as in claim 2, wherein said medicant includes an anesthetic.

11. A patch for transdermal application of a medicant as in claim 2, wherein said medicant includes at least one anti-inflammatory agent.

12. A patch for transdermal application of a medicant as in claim 2, wherein said medicant includes at least one anti-infective agent.

13. A patch for transdermal application of a medicant for use with a first electrode comprising:
    a patch border portion disposed about an aperture;
    said border portion including a patch electrode disposed about said aperture and disposed to be in electrical communication with said medicant.

14. A patch for transdermal application of a medicant as in claim 13, further comprising a liftable portion disposed over said aperture.

15. A patch for transdermal application of a medicant as in claim 13, wherein said liftable portion is removable.

16. A patch for transdermal application of a medicant as in claim 13, wherein said liftable portion has a periphery and said liftable portion is attached to said patch border along at least one portion of said periphery.

17. A patch for transdermal application of a medicant as in claim 13, wherein said patch liftable portion is transparent.

18. A patch for transdermal application of a medicant as in claim 13, wherein said patch liftable portion is non-adherent to skin.

19. A patch for transdermal application of a medicant as in claim 13, wherein said patch border portion is contiguous.

20. A patch for transdermal application of a medicant as in claim 13, wherein said patch border portion includes non-contiguous border segments.

21. A patch for transdermal application of a medicant as in claim 13, wherein said medicant includes an analgesic.

22. A patch for transdermal application of a medicant as in claim 13, wherein said medicant includes an anesthetic.

23. A patch for transdermal application of a medicant as in claim 13, wherein said medicant includes at least one anti-inflammatory agent.

24. A patch for transdermal application of a medicant as in claim 13, wherein said medicant includes at least one anti-infective agent.

25. A method for performing a field block anesthetic about an epidermal target site having a border region disposed about said target site, the method comprising the step of:
    delivering an anesthetic substance in said border region while not delivering said anesthetic substance to said target site, and while not injecting said anesthetic substance under pressure into said epidermal border region.

26. A method for performing a field block anesthetic about an epidermal target site as in claim 25, wherein said anesthetic substance delivery step is accomplished without mechanically penetrating into said epidermal border region.

27. A method for performing a field block anesthetic about an epidermal target site as in claim 25, wherein said anesthetic substance delivery step is accomplished iontophoretically.

28. A method for performing a field block anesthetic about an epidermal target site having a border region disposed about said target site, the method comprising the step of:
    iontophoretically delivering an anesthetic substance in said border region while not iontophoretically delivering said anesthetic substance to said target site.

29. A method for performing a field block anesthetic as in claim 28, further comprising observing said target site while delivering said anesthetic substance.

30. A method for performing a field block anesthetic as in claim 28, wherein said iontophoretically delivery step includes providing a liftable cover over said target site and lifting said liftable cover during said iontopheretic delivery step and observing said target site.

31. A method for performing a field block anesthetic as in claim 30, wherein said iontophoretically delivery step includes providing a non-adherent cover over said target site and lifting step does not include adhesively pulling of said target site.

32. A method for performing a field block anesthetic as in claim 28, wherein said iontophoretically delivery step includes providing a transparent cover over said target site and observing said target site during said iontophoretically delivery step.

33. A method for performing a field block anesthetic as in claim 28, wherein the method includes performing an invasive medical procedure on said target site during said iontophoretically delivery step.

34. A method for managing pain during an epidermally invasive procedure at an epidermal target site having a border region disposed about the target site, the method comprising the steps of:
   performing an anesthetic field block by iontophoretically delivering an anesthetic substance in said border region while not iontophoretically delivering said anesthetic substance to said target site; and
   performing said epidermally invasive procedure.

35. A method for managing pain as in claim 34, wherein said performing anesthetic field block step is performed before said epidermally invasive procedure step.

36. A method for managing pain as in claim 34, wherein said performing anesthetic field block step is performed after said epidermally invasive procedure step.

37. A method for managing pain as in claim 34, wherein said performing anesthetic field block step is performed both before and after said epidermally invasive procedure step.

38. A method for managing pain as in claim 34, wherein said epidermally invasive procedure step is selected from the group of procedures consisting of:
   incisions, drainage, excisions, punctures, skin abrasions, mucus membrane abrasions, and deeper tissue anesthetic injections.

39. A method for managing inflammation at an inflamed epidermal target site having a border region disposed about the target site, the method comprising surrounding the inflamed site by iontophoretically delivering at least one anti-inflammatory agent.

40. A method for managing inflammation at an inflamed epidermal target site as in claim 39, wherein said at least one anti-inflammatory agent is selected from the group consisting of salicylates and corticosteroids.

41. A method for managing infection at an epidermal target site having a border region disposed about the target site, the method comprising surrounding the inflamed site by iontophoretically delivering at least one anti-infective agent.

42. A method for enhancing wound healing at an epidermal target site having a border region disposed about the target site, the method comprising surrounding the target site with electrical potential applied in said border region.

43. A method for performing a field block anesthetic about an epidermal target site having a border region disposed about said target site, the method comprising the step of:
   actively delivering an anesthetic substance in said border region while not actively delivering said anesthetic substance to said target site, and while not injecting said anesthetic substance under pressure into said epidermal border region.

* * * * *